United States Patent [19]

Bastian et al.

[11] 3,991,066
[45] Nov. 9, 1976

[54] 1,3,4,9b-TETRAHYDRO-5-METHYL-2H-INDENO[1,2-c]PYRIDINES

[75] Inventors: Jean-Michel Bastian, Therwil; Anton Ebnöther, Arlesheim; Erwin Rissi, Basel, all of Switzerland

[73] Assignee: Sandoz Ltd., Basel, Switzerland

[22] Filed: May 16, 1975

[21] Appl. No.: 578,103

Related U.S. Application Data

[63] Continuation of Ser. No. 352,956, April 20, 1973, abandoned, which is a continuation-in-part of Ser. No. 218,509, Jan. 17, 1972, Pat. No. 3,749,729.

[30] Foreign Application Priority Data

Jan. 26, 1971 Switzerland.......................... 1121/71

[52] U.S. Cl.............................. 260/293.54; 424/267
[51] Int. Cl.²...................................... C07D 221/16
[58] Field of Search................................ 260/293.54

[56] References Cited
UNITED STATES PATENTS 3,678,058   7/1972   Ebnother et al............... 260/293.54

Primary Examiner—G. Thomas Todd
Attorney, Agent, or Firm—Gerald D. Sharkin; Robert S. Honor

[57] ABSTRACT

The invention concerns novel indenopyridine derivatives of the formula:

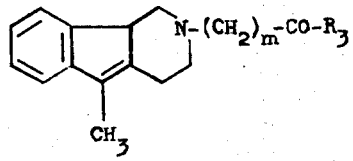

wherein $m$ is 1, 2, 3 or 4, and
$R_3$ is an —O—$R_4$ group,
wherein $R_4$ is alkyl of 1 to 5 carbon atoms, phenyl or phenylalkyl, wherein the alkyl radical is of 1 to 4 carbon atoms, or an

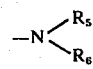

group,
wherein each of
$R_5$ and $R_6$ is, independently, hydrogen, alkyl of 1 to 5 carbon atoms, cycloalkyl of 3 to 7 carbon atoms, phenyl or phenyl-alkyl, wherein the alkyl radical is of 1 to 4 carbon atoms, or
$R_5$ and $R_6$ together with the nitrogen atom form a saturated 5- or 6-membered heterocyclic ring, the heterocycle being selected from heterocycles containing 1 nitrogen atom, 1 nitrogen atom and 1 oxygen atom, and 1 nitrogen atom and a further nitrogen atom substituted by an alkyl radical of 1 to 4 carbon atoms, useful as anti-aggressives and in the treatment of excitation conditions.

3 Claims, No Drawings

1,3,4,9b-TETRAHYDRO-5-METHYL-2H-INDENO[1,2-c]PYRIDINES

This is a continuation of application Ser. No. 352,956, filed Apr. 20, 1973, now abandoned, which in turn is a continuation-in-part of application Ser. No. 218,509, filed Jan. 17, 1972 now U.S. Pat. No. 3,749,729.

This application is a continuation in part of our U.S. copending application Ser. No. 218,509 filed Jan. 17, 1972.

This invention relates to novel indenopyridine derivatives.

In accordance with this invention there are provided new compounds of formula I,

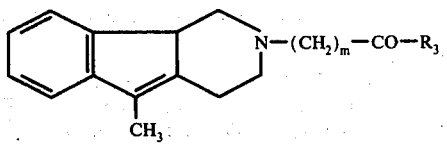

wherein m is 1, 2, 3 or 4, and
R$_3$ is an —O—R$_4$ group,
  wherein R$_4$ is alkyl of 1 to 5 carbon atoms, phenyl or phenylalkyl, wherein the alkyl radical is of 1 to 4 carbon atoms, or an

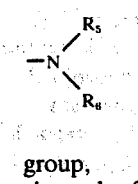

group,
wherein each of
  R$_5$ and R$_6$ is, independently, hydrogen, alkyl of 1 to 5 carbon atoms, cycloalkyl of 3 to 7 carbon atoms, phenyl or phenylalkyl, wherein the alkyl radical is of 1 to 4 carbon atoms, or
  R$_5$ and R$_6$ together with the nitrogen atom form a saturated 5- or 6-membered heterocyclic ring, the heterocycle being selected from heterocycles containing 1 nitrogen atom, 1 nitrogen atom and 1 oxygen atom, and 1 nitrogen atom and a further nitrogen atom substituted by an alkyl radical of 1 to 4 carbon atoms.

Further, in accordance with the invention a compound of formula I may be obtained by a process comprising
a. reacting the compound of formula III

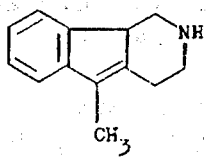

with a compound of formula IV,

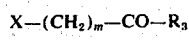

wherein m and R$_3$ are as defined above, and
X is the acid radical of a reactive ester, and, if desired, converting the resulting compound of formula I into acid addition salt form, or
b. preparing a compound of formula Ic,

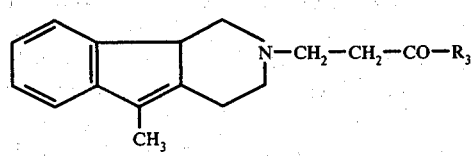

wherein R$_3$ is as defined above,
by reacting the compound of formula III with a vinylcarbonyl derivative of formula V,

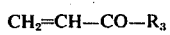

wherein R$_3$ is as defined above,
and, if desired, converting the resulting compound of formula Ic into acid addition salt form.

When R$_4$, R$_5$ and R$_6$ denote alkyl radicals, these preferably signify the ethyl or tert.butyl radical.

When R$_5$ and R$_6$ together with the nitrogen atom form a heterocycle, this is preferably the piperidine, pyrrolidine, N'(lower)alkylpiperazine or morpholine ring.

Process (a) may, for example, be effected by reacting the compound of formula III, in free base or acid addition salt form, with a compound of formula IV, wherein X preferably signifies chlorine, bromine, the methyl- or p-toluenesulphonic acid radical, preferably in an inert solvent, e.g. in an aromatic hydrocarbon such as toluene or benzene, or in a chlorinated hydrocarbon such as chloroform or carbon tetrachloride, or in a di(lower)alkyl amide of a lower carboxylic acid, such as dimethyl formamide, or a lower alcohol. The reaction may be carried out in the presence of an acid-binding agent, e.g. an alkali metal carbonate such as sodium or potassium carbonate, or a tertiary base such as triethylamine, or an excess of the compound of formula III. A suitable reaction temperature is from 50° C to the boiling temperature of the reaction mixture.

Process (b) may, for example, be effected by reacting the compound of formula III, in free base or acid addition salt form, with a compound of formula V in an inert solvent, e.g. a lower alcohol such as ethanol. A suitable reaction temperature is from 20° C to the boiling temperature of the reaction mixture. The reaction is conveniently effected in the presence of a catalytic amount of a strong basic condensation agent, e.g. benzyl trimethyl ammonium hydroxide.

The free base forms of the compounds of formula I may be converted into acid addition salts, and acid addition salts into free base forms, in conventional manner.

Insofar as the production of the starting materials is not described, the compounds are known or may be prepared by known processes, or in a manner analogous to the processes described herein or to known processes.

The compounds of formula I or their salts have hitherto not been described in the literature. They exhibit interesting pharmacodynamic properties and are therefore indicated for use as medicaments.

The compounds of formula I or pharmaceutically acceptable acid addition salts thereof are useful because they possess pharmacological activity in animals.

In particular, the compounds are useful anti-aggressives, as indicated by the isolation-induced aggression test in mice upon intraperitoneal administration of 0.1 mg/kg to 3 mg/kg of the compounds.

For the above-mentioned use, the dosage administered will, of course, vary depending upon the compound employed, mode of administration and treatment desired. However, in general, satisfactory results are obtained when administered at a daily dosage of from 0.1 to 3 mg/kg animal body weight, preferably given in divided doses 2 to 3 times a day, or in sustained release form. For the larger mammals, the total daily dosage is in the range of from about 10 to about 80 mg, and dosage forms suitable for oral administration comprise from about 3.3 to about 40 mg of the compound admixed with a solid or liquid pharmaceutical carrier diluent.

The compounds of formula I or pharmaceutically acceptable acid addition salts thereof are furthermore useful in the treatment and prophylaxis of excitation conditions, as indicated by the depressive effect which they exhibit on the central nervous system, such as shown in the standard light barrier motility test in mice upon intraperitoneal administration of 1 mg/kg to 30 mg/kg of the compounds. For such use, the dosage administered will, of course, vary depending upon the compound employed, mode of administration and treatment desired. However, in general, satisfactory results are obtained when administered at a daily dosage of from about 1 to about 30 mg/kg animal body weight, preferably given in divided doses 2 to 3 times a day, or in sustained release form. For the larger mammals, the total daily dosage is in the range of from about 50 to about 150 mg, and dosage forms suitable for oral administration comprise from about 15 to about 75 mg of the compound admixed with a solid or liquid pharmaceutical carrier or diluent.

Compounds having particularly interesting anti-agressive properties include: 5-methyl-1,3,4,9b-tetrahydro-2H-ideno[1,2-c]-pyridine-3-propionic acid ethyl ester.

The compounds of formula I may be administered in pharmaceutically acceptable acid addition salt form. Suitable such salt forms include mineral acid salts, such as the hydrochloride, hydrobromide and sulphate, and organic acid salts, such as the methane- and benzene-sulphonate.

The invention also provides a pharmaceutical composition comprising as active agent a compound of formula I in pharmaceutically acceptable acid addition salt form, or in free base form, in association with a pharmaceutical carrier or diluent.

Such compositions may be prepared by conventional techniques to be in the form of, for example, capsules, tablets, suppositories, suspensions or solutions, for enteral or parenteral administration. Aside from the usual pharmaceutical diluents or carriers, e.g. water, alcohols, natural or hardened oils and waxes, these pharmaceutical compositions may contain suitable preserving, stabilizing, wetting, solubilizing, sweetening, flavouring or colouring agents.

In the following non-limitative Examples all temperatures are indicated in degrees Centigrade.

EXAMPLE 1:
1,3,4,9b-Tetrahydro-5-methyl-2H-indeno[1,2-c]pyridine-2-acetic acid methyl ester [process variant a)]

A solution of 15.3 g of bromoacetic acid methyl ester in 50 cc of dimethyl formamide is added dropwise at 60° while stirring to a mixture of 18.5 g of 1,3,4,9b-tetrahydro-5-methyl-2H-indeno[1,2-c]pyridine and 41.4 g of potassium carbonate in 200 cc of dimethyl formamide. The reaction mixture is allowed to react at 60° for 1 hour, is poured on ice water and is extracted thrice with chloroform. The extracts are dried and completely concentrated by evaporation, the residue is dissolved in 50 cc of methanol, and the calculated amount of hydrochloric acid in ethanol is added. After the addition of ether, 1,3,4,9b-tetrahydro-5-methyl-2H-indeno [1,2-c]pyridine-2-acetic acid methyl ester crystallizes as hydrochloride and is recrystallized twice from ethanol for further purification. The hydrochloride has a M.P. of 184°–185°.

The following compounds are prepared employing the process which is exemplified in Example 1:

5-(1,3,4,9b-tetrahydro-5-methyl-2H-indeno[1,2-c]pyridine-2-yl)-valeric acid phenyl ester;
5-(1,3,4,9b-tetrahydro-5-methyl-2H-indeno[1,2-c]pyridin-2-yl)-N,N-dicyclo-hexyl valeric acid amide;
5-(1,3,4,9b-tetrahydro-5-methyl-2H-indeno[1,2-c]pyridin-2-yl)-N,N-diphenyl valeric acid amide;
5-(1,3,4,9b-tetrahydro-5-methyl-2H-indeno[1,2-c]pyridin-2-yl)-N,N-dibenzyl valeric acid amide;
5-(1,3,4,9b-tetrahydro-5-methyl-2H-indeno[1,2-c]pyridin-2-yl-valeric acid morpholide; and
1-(3-methyl-imidazolidinyl)-5-(1,3,4,9b-tetrahydro-5-methyl-2H-indeno[1,2-c]pyridin-2-yl)-pentan-1-one.

EXAMPLE 2:
4-(1,3,4,9b-Tetrahydro-5-methyl-2H-indeno[1,2-c]-pyridin-2-yl)butyric acid ethyl ester 1,3,4,9b-Tetrahydro-5-methyl-2H-indeno[1,2-c]-pyridine and 4-bromobutyric acid ethyl ester are reacted in accordance with the process described in Example 1. The hydrochloride of the title compound has a M.P. of 186°–188° from ethanol/acetone.

EXAMPLE 3:
5-(1,3,4,9b-Tetrahydro-5-methyl-2H-indeno[1,2-c]pyridin-2-yl) valeric acid amide 1,3,4,9b-Tetrahydro-5-methyl-2H-indeno[1,2-c]pyridine and 5-chlorovaleric acid amide are reacted in accordance with the process described in Example 1. Reaction period 19 hours at 60°. The hydrochloride of the title compound has a M.P. of 194°–196° from ethanol.

EXAMPLE 4:
1,3,4,9b-Tetrahydro-5-methyl-2H-indeno[1,2-c]pyridine acetamide 1,3,4,9b-Tetrahydro-5-methyl-2H-indeno[1,2-c]pyridine and chloroacetamide are reacted in accordance with the process described in Example 1. Reaction period four hours at 60°. M.P. of the title compound 167°–168° from acetone.

EXAMPLE 5:
3-(1,3,4,9b-Tetrahydro-5-methyl-2H-indeno[1,2-c]pyridin-2-yl) propionic acid ethyl ester [process variant b)]

A mixture of 12.5 g of 1,3,4,9b-tetrahydro-5-methyl-2H-indeno[1,2-c]pyridine and 8.8 cc of acrylic acid ethyl ester is heated to 80° in 100 cc of ethanol for 3 hours, and is subsequently evaporated to dryness. The residue is distilled in a high vacuum, whereby the title compound distils over at 161°–165°/0.1 mm of Hg.

The base is converted into the hydrochloride by dissolving the distillate in ethanol and adding the calculated amount of hydrochloric acid in ethanol. The resulting crude hydrochloride is again recrystallized from ethanol. M.P. 183°–184° (decomp.).

EXAMPLE 6:
3-(1,3,4,9b-Tetrahydro-5-methyl-2H-indeno[1,2-c]pyridin-2-yl) propionic acid amide A mixture of 18.5 g of 1,3,4,9b-tetrahydro-5-methyl-2H-indeno[1,2-c]pyridine and 7.1 g of acrylamide in 250 cc of ethanol is boiled at reflux for 6 hours. The reaction mixture is evaporated to dryness, and the resulting title compound is recrystallized from ethanol. M.P. 169°–170°.

EXAMPLE 7:
3-(1,3,4,9b-Tetrahydro-5-methyl-2H-indeno[1,2-c]pyridin-2-yl)-N-methylpropionic acid amide 1,3,4,9b-Tetrahydro-5-methyl-2H-indeno[1,2-C]pyridine and N-methyl acrylamide are reacted in accordance with the process described in Example 6. Reaction period 15 hours. M.P. of the hydrochloride of the title compound 200°–201° from ethanol.

EXAMPLE 8:
3-(1,3,4,9b-Tetrahydro-5-methyl-2H-indeno[1,2-c]pyridin-2-yl)-N,N-dimethylpropionic acid amide 1,3,4,9b-Tetrahydro-5-methyl-2H-indeno[1,2-c]pyridine and N,N-dimethyl acrylamide are reacted in accordance with the process described in Example 6. Reaction period 7 hours. M.P. of the hydrochloride of the title compound 219°–221° from ethanol.

EXAMPLE 9:
3-(1,3,4,9b-Tetrahydro-5-methyl-2H-indeno[1,2-c]pyridin-2-yl)-N-propylpropionic acid amide 1,3,4,9b-Tetrahydro-5-methyl-2H-indeno[1,2-c]pyridine and N-propyl acrylamide are reacted in accordance with the process described in Example 6. Reaction period 20 hours. M.P. of the hydrochloride of the title compound 196°–197° from ethanol (decomp.).

EXAMPLE 10:
N-n-Butyl-3-(1,3,4,9b-tetrahydro-5-methyl-2H-indeno [1,2-c]pyridin-2-yl) propionic acid amide 1,3,4,9b-Tetrahydro-5-methyl-2H-indeno[1,2-c]pyridine and N-n-butyl acrylamide are reacted in accordance with the process described in Example 6. Reaction period 14 hours. M.P. of the hydrochloride of the title compound 193°–194° from ethanol (decomp.).

EXAMPLE 11:
N-Cyclohexyl-3-(1,3,4,9b-tetrahydro-5-methyl-2H-indeno [1,2-c]pyridin-2-yl) propionic acid amide 1,3,4,9b-Tetrahydro-5-methyl-2H-indeno[1,2-c]pyridine and N-cyclohexyl acrylamide are reacted in accordance with the process described in Example 6. Reaction period 8 hours. M.P. of the title compound 162.5°–163.5° from acetone.

EXAMPLE 12:
3-(1,3,4,9b-Tetrahydro-5-methyl-2H-indeno[1,2-c]pyridin-2-yl) propionic acid piperidide 1,3,4,9b-Tetrahydro-5-methyl-2H-indeno[1,2-c]pyridine and acrylic acid piperidide are reacted in accordance with the process described in Example 6. Reaction period nine hours. M.P. of the hydrochloride of the title compound 219°–221° from ethanol (decomp.).

EXAMPLE 13:
N-Benzyl-3-(1,3,4,9b-tetrahydro-5-methyl-2H-indeno [1,2-c]pyridin-2-yl) propionic acid amide 1,3,4,9b-Tetrahydro-5-methyl-2H-indeno[1,2-c]pyridine and N-benzyl acrylamide are reacted in accordance with the process described in Example 6. Reaction period 8 hours. M.P. of the hydrochloride of the title compound 211°–212.5° from ethanol (decomp.).

EXAMPLE 14:
3-(1,3,4,9b-Tetrahydro-5-methyl-2H-indeno[1,2-c]pyridin-2-yl)-N-phenylpropionic acid amide 1,3,4,9b-Tetrahydro-5-methyl-2H-indeno[1,2-c]pyridine and N-phenyl acrylamide are reacted in accordance with the process described in Example 6. Reaction period 4 hours. M.P. of the hydrochloride of the title compound 207°–209° from 95% ethanol.

EXAMPLE 15:
3-(1,3,4,9b-Tetrahydro-5-methyl-2H-indeno[1,2-c]-pyridin-2-yl)propionic acid benzyl ester A mixture of 12.5 g of 1,3,4,9b-Tetrahydro-5-methyl-2H-indeno[1,2-c]pyridine and 10 g acrylic acid ethyl ester are heated in 100 ml of ethanol for 3 hours at 80° C and then evaporated to dryness. The title compound is obtained as a colourless oil after distillation under a vacuum of 0.1 Torr.

What is claimed is:
1. The compound which is N-Cyclohexyl-3-(1,3,4,9b-tetrahydro-5-methyl-2H-indeno pyridin-2-yl) propionic acid amide.
2. The compound which is N-Benzyl-3-(1,3,4,9b-tetrahydro-5-methyl-2H-indeno pyridin-2-yl) propionic acid amide.
3. The compound which is 3-(1,3,4,9b-Tetrahydro-5-methyl-2H-indeno pyridin-2-yl-N-phenylpropionic acid amide.

* * * * *